United States Patent [19]
Ikematsu

[11] Patent Number: 6,056,922
[45] Date of Patent: May 2, 2000

[54] BILAYER MEMBRANE DEVICE

[75] Inventor: Mineo Ikematsu, Tsuchiura, Japan

[73] Assignee: Sanyo Electric Co., Ltd, Osaka, Japan

[21] Appl. No.: 08/865,370

[22] Filed: May 29, 1997

[30]  Foreign Application Priority Data

May 30, 1996 [JP] Japan .................................. 8-136482
Apr. 25, 1997 [JP] Japan .................................. 9-109841

[51] Int. Cl.$^7$ .................................................. G01N 27/00
[52] U.S. Cl. ........................ 422/68.1; 422/82.01; 422/88; 422/98; 436/149
[58] Field of Search ........................... 204/418; 436/149; 422/68.1, 82.01, 88, 98

[56]  References Cited

U.S. PATENT DOCUMENTS

| H201 | 1/1987 | Yager ....................................... 436/151 |
| 5,637,201 | 6/1997 | Raguse et al. ........................... 204/418 |

FOREIGN PATENT DOCUMENTS 9407593  4/1994  WIPO .

OTHER PUBLICATIONS

E.–L. Florin, et al. "Painted Supported Lipid Membranes", Biophysical Society, vol. 64, Feb. 1993, pp. 375–383.

Karsten Seifert, et al., "Charge transport by ion translocating membrane proteins on solid supported membranes", Biophysical Society, vol. 64, Feb. 1993, pp. 384–391.

Claus Duschl, "Biologically Addressable Monolayer Structures Formed by Templates of Sulfur–Bearing Molecules", Biophysical Society, vol. 67, Sep. 1994, pp. 1229–1237.

Martin Stelzle, et al., "Sensitive detection of protein adsorption to supported lipid bilayers by frequency–dependent capacitance measurements and microelectrophoresis", 1989 Elsevier Science Publishers B.V., pp. 135–142.

Plant, Al et al. Anal. Biochem. 226: 342–348, 1995.
King, TE. et al. BBRC, 49(6): 1433–1437, 1972.
Stelzle, M et al. BBA 981: 135–142, 1989.
Seifert, K et al. Biophys. J 64: 384–391, 1993.

*Primary Examiner*—Sheela Huff
*Attorney, Agent, or Firm*—Loeb & Loeb, LLP

[57]  ABSTRACT

An alkanethiol monolayer membrane is formed on a substrate having an Au layer using Au—S bonding, and a second layer constructed by a monolayer lipid membrane is formed on its surface to form a BLM. A gel layer is formed using agarose on the side of the BLM having the second monolayer lipid layer. In addition, a polymer layer is formed using the amino acid poly-L-lysine between the surface of the monolayer lipid membrane and the gel layer to immobilize the BLM. The use of this supporting constitution for holding and immobilizing the membrane extends the life-span of the BLM, while the gel layer keeps the electrolyte solution required for maintaining flexibility of the membrane and activating protein on the surface of the BLM. In addition, a BLM having a life-span of one month or more is obtained by arranging a membrane supporting portion that minimizes lifting of the membrane molecules due to buoyancy above the BLM arranged upright in an aqueous system.

18 Claims, 11 Drawing Sheets

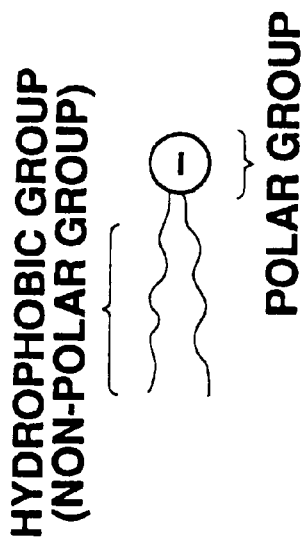
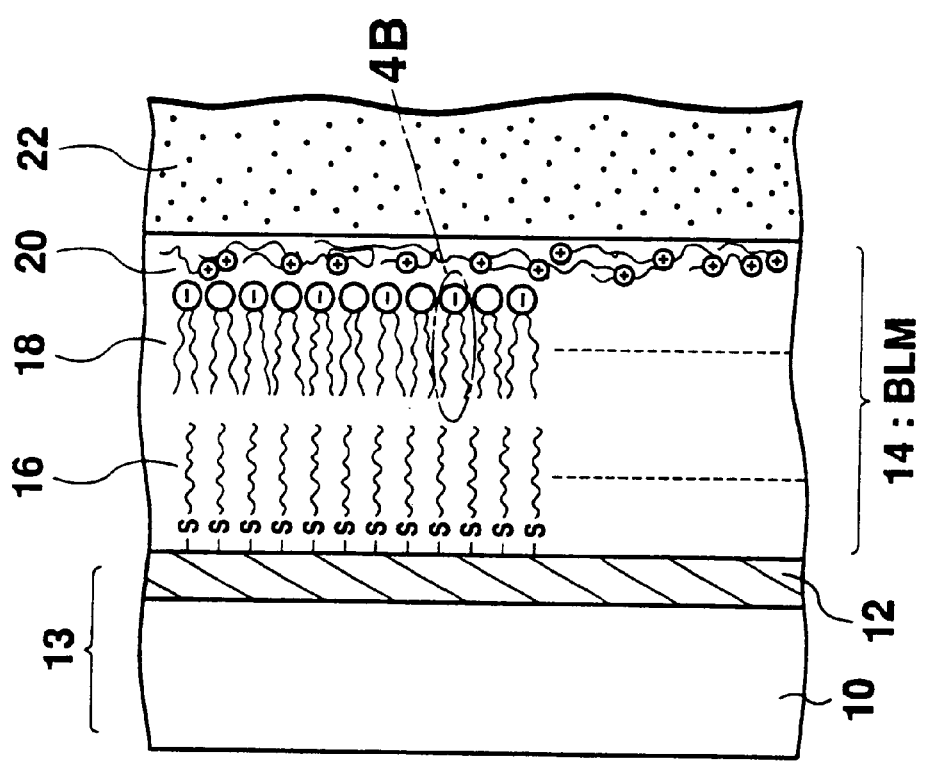

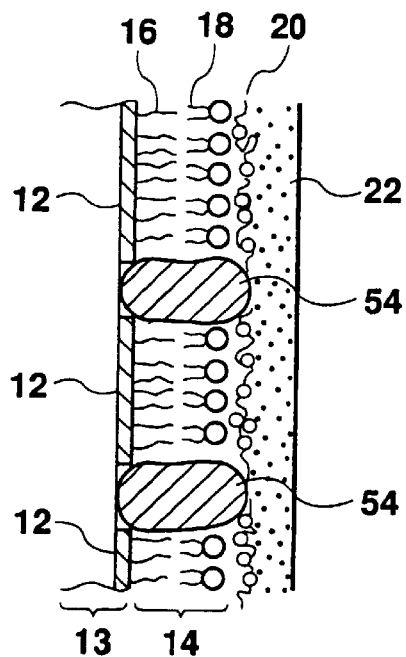
Fig. 14
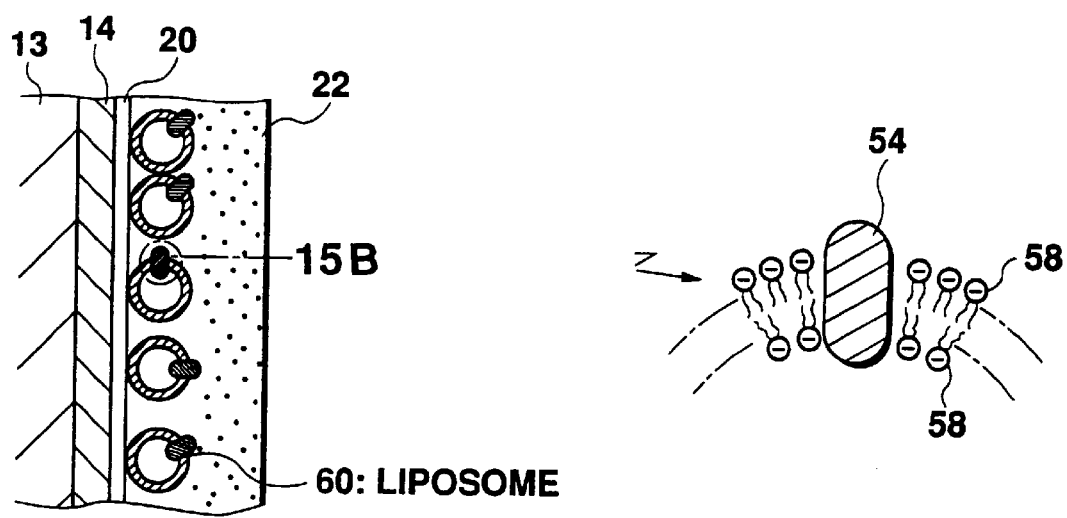
Fig. 15A
Fig. 15B

BILAYER MEMBRANE DEVICE

BACKGROUND OF THE INVENTION

1. Field of the Invention

The present invention relates to a bilayer membrane device, for example, to a bilayer membrane device having a bilayer membrane which is constructed of two molecular layers (i.e. monolayers) and holds protein or the like and has a constitution similar to that of an organic cell membrane, and having excellent stability that enables it to be used when causing a held protein to function within a bilayer membrane or during measurement of that function.

2. Description of the Related Art

Various proposals have been made in the past for producing a bilayer membrane having a constitution similar to that of an organic cell membrane. Protein function research has been conducted in which protein is caused to function in the same manner as in a cell membrane by using this bilayer membrane. Moreover, bio-functional device are expected to be produced that utilize the functions of bilayer membrane and proteins.

In the case of devices having an artificial bilayer membrane that have been reported in the past, monolayer is used that is composed of polar groups and hydrophobic groups. In an aqueous solution, a Teflon substrate in which a hole is provided in the center is arranged upright as shown in FIG. 1, and two layers of monolayer lipid membranes are formed in the hole portion of this Teflon substrate with the polar groups facing to the outside and hydrophobic groups facing to the inside as shown in FIG. 2, resulting in the constitution of a bilayer membrane.

However, since the bilayer membranes produced in this manner are adhered only by their mutual intermolecular forces, the bilayer membrane structure ends up being quickly destroyed due to impact or other excessive outside forces. In addition, even when allowed to stand undisturbed, there is the problem of bilayer membrane structures like those shown in the drawings only being maintainable for several hours.

With this in mind, it has been proposed to form a bilayer membrane on the surface of support substrate for the purpose of producing a bilayer membrane having higher stability. In the example shown in FIG. 3A, the polar groups of one of the lipid monolayer are adsorbed onto a support substrate 3 made of glass or such material arranged horizontally in an aqueous solution to form monolayer membrane 2. Moreover, a second layer of monolayer membrane 2 is formed on this monolayer membrane 2 by adsorbing lipid single molecules to obtain a bilayer membrane.

In addition, in another example, stearylmercaptan, for example, is introduced onto the surface of substrate 6 formed by Au as shown in FIG. 3B, after which alkanethiol monolayer membrane 4 is formed on the substrate surface by Au—S bonding. Monolayer lipid membrane 2 is further adsorbed onto the resulting monolayer membrane 4 to form a bilayer membrane.

However, even in the case of a bilayer membrane formed by using a support substrate as described above, the length of time during which its bilayer membrane structure can be maintained when allowed to stand undisturbed in an aqueous solution is only in the range of several hours to just over ten hours. Thus, it is difficult to perform processing such as inserting protein into the resulting bilayer membrane, thus causing this membrane to lack practicality as a device. Consequently, there is a need to obtain a bilayer membrane having even greater stability.

SUMMARY OF THE INVENTION

In order to solve the above-mentioned problems, an object of the present invention is to provide a device that enables a bilayer membrane structure to be maintained for a longer time.

In order to achieve the above-mentioned object, the bilayer membrane device as claimed in the present invention is characterized as described below.

(1) First, the bilayer membrane device is a device in which a bilayer membrane is formed on a substrate, and is characterized in that this bilayer membrane is either directly or indirectly covered with a gel layer. The stability of the bilayer membrane is improved by covering the bilayer membrane with a gel layer in this manner. In addition, it is possible to keep water around the bilayer membrane by using a gel layer, in particular using hydrogel as a gel layer. For example, an electrolytic solution required for maintaining flexibility of a bilayer membrane or the function of a protein introduced into this membrane is kept around the bilayer membrane, thereby making it possible to supply electrolytic solution to the membrane and the protein. Moreover, disturbance of the membrane is prevented as a result of the gel layer interrupting aqueous movement on the surface of the bilayer membrane. Accordingly, the function of the gel layer in terms of keeping electrolytic solution ultimately contributes to improved stability of the membrane.

Moreover, in addition to the above-mentioned constitution, the present invention is characterized in that a polymer layer is formed between a bilayer membrane and a gel layer. The stability of the bilayer membrane is further improved by employing this type of constitution wherein a bilayer membrane is covered with a polymer layer, and this is then further covered with a gel layer. The reason for the improvement in stability of the membrane because covering with a polymer layer is thought to be the result of strong interaction between the polar groups of the above-mentioned polymer layer and the polar groups of the monolayer membrane on the polymer layer side in a case where the monolayer membrane on the polymer layer side has polar groups, and especially in the case where the polar groups of the monolayer membrane opposing the polymer layer and the polar groups of the polymer layer are opposite.

Furthermore, in one example of the above-mentioned bilayer membrane device, the polymer layer is characterized by being an amino acid, specifically polylysine, and the gel layer is characterized by being a sugar, specifically agarose gel. The use of these materials for the polymer layer and gel layer will enable the production of an environment that closely approximates that in the biological conditions around the bilayer membrane, thereby allowing the protein to function adequately.

Preferably, the bilayer membrane used in the above-mentioned device is characterized by being composed of an alkanethiol monolayer membrane, in which polar groups are bonded to a metal on a substrate surface, and a monolayer lipid membrane, arranged on the alkanethiol monolayer membrane towards the hydrophobic groups. An extremely stable first layer of a bilayer membrane is formed on the substrate surface by bonding molecules of the first layer of the bilayer membranes to the substrate. Thus, the stability of the second layer of the monolayer membrane, for example, the monolayer lipid membrane, formed by adsorbing to the first monolayer membrane of the substrate surface by intermolecular force is improved, which results in the obtaining of a stable bilayer membrane.

(2) Another constitution of the present invention is a device having a bilayer membrane device formed on a substrate characterized by having a membrane supporting portion provided at least on the upper side of the above-mentioned substrate arranged upright in an aqueous system for supporting the upper portion of a bilayer membrane in an aqueous system by extending in the direction of membrane width of a bilayer membrane device.

In addition, the above-mentioned membrane supporting portion is characterized by having a length equal to or greater than the membrane thickness of the bilayer membrane and in that lifting of the above-mentioned bilayer membrane arranged upright in an aqueous system being inhibited by this membrane supporting portion. This membrane supporting portion may be provided on both upper and lower sides of the substrate.

Moreover, the side of the aqueous system of this bilayer membrane is characterized by being covered with a gel layer. It is also possible to form a polymer layer between the bilayer membrane and the gel layer. A sugar is used for the above-mentioned gel layer and an amino acid is used for the above-mentioned polymer layer.

In a bilayer membrane device arranged upright in an aqueous system, separation of the monolayer membrane of the upper portion of the membrane occurs easily due to the monolayer layer of the bilayer membrane facing the side of the aqueous system being subjected to the effects of buoyancy. Therefore, the stability of the bilayer membrane can be further improved by preventing separation of the membrane molecules and preventing the molecules from flowing into the aqueous system by providing a membrane supporting portion on the upper portion of the membrane as described above.

(3) Yet another constitution of the present invention is a bilayer membrane device having a bilayer membrane characterized by covering with a gel layer, regardless of the presence or absence of a substrate that supports the bilayer membrane. Agarose gel or hydrogel may be used for the gel layer.

In addition, a bilayer membrane is formed in gap regions of a metal substrate having apertures, a substrate with apertures and having a metal film on its surface, or a substrate provided on its surface with a metal material of a predetermined pattern having apertures, and protein is introduced into the bilayer membrane in these gap regions. In addition to being able to obtain a bilayer membrane having a high degree of stability, it is easy to later insert protein into the bilayer membrane formed in the gap regions by using the above-mentioned substrate. Thus, use of the above-mentioned constitution provides greater reliability in enabling the present invention to actually function as a bilayer membrane device, namely a bio-functional device.

(4) Moreover, another constitution of the present invention is characterized in that, a liposome is formed on a bilayer membrane in a device having a bilayer membrane as described above, said liposome being covered by the above-mentioned gel layer. Here, the environment in which the liposomes are placed can be made to more closely approximate that of actual biological conditions by covering the liposomes with the gel layer. Thus, it is possible to obtain a bilayer membrane device that enables protein to function normally and with greater stability. In addition, a bilayer membrane device having a longer life-span and excellent stability is obtained since the bilayer membrane and liposomes can be immobilized by a gel layer.

As has been explained above, according to each of the bilayer membrane devices of the present invention, the stability of the bilayer membrane formed can be improved by a gel layer or the combination of a gel layer and polymer layer, or by a membrane supporting portion or the combination of a membrane supporting portion and a gel layer and so forth, thereby significantly improving the practicality of the device. Thus, it is possible to introduce proteins into the device and conduct research on protein functions using this device or produce devices that utilize these protein functions.

BRIEF DESCRIPTION OF THE DRAWINGS

FIG. 4 is a drawing indicating the constitution of a bilayer membrane device according to a first embodiment of the present invention.

FIG. 14 is a drawing indicating another example of the constitution of a third embodiment of the present invention.

FIG. 15 is a drawing indicating the constitution of a bilayer membrane device according to a fourth embodiment of the present invention.

DESCRIPTION OF PREFERRED EMBODIMENTS

Figure 2B:
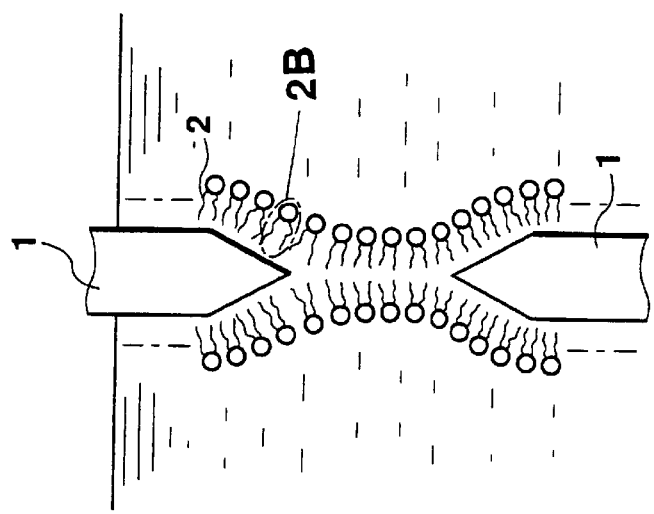
FIGS. 1 and 2 are drawings indicating the constitution of a bilayer membrane device of the prior art.
Figure 2A:
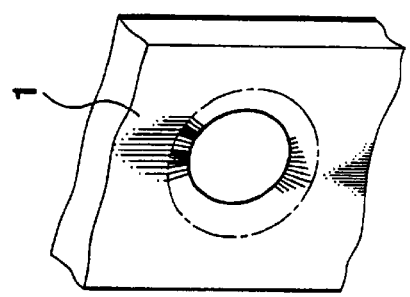

The following provides an explanation of the preferred embodiments of the present invention with reference to the attached drawings, in which the same reference numerals denote the same structures.

Embodiment 1

[Device Constitution]

A bilayer membrane device of the present invention has a bilayer membrane for holding protein or the like. The bilayer membrane has a bilayer structure which comprises monolayer membranes of organic molecule, in particular, of a monolayer lipid membrane and a monolayer consisted of organic molecules having alkyl chain (i.e., lipid bilayer membrane).

FIG. 4 shows the constitution of a first embodiment containing the above bilayer membrane device. In FIG. 4, Au layer 12 is formed on the surface of glass substrate 10 to compose a substrate 13. On the surface of Au layer 12, metal and the mercapto groups (—SH) of stearylmercaptan [HS(CH$_2$)$_{17}$CH$_3$] form Au—S bonds, and alkanethiol monolayer [SC$_n$H$_{2n+1}$; n=18, S(CH$_2$)$_{17}$CH$_3$) in the present embodiment] monolayer membrane 16 is formed by this bonding.

Moreover, lipid, and in this case soybean phospholipid, is adsorbed onto the alkanethiol monolayer membrane 16 by intermolecular force with its hydrophobic groups facing said alkanethiol monolayer membrane 16, resulting in the formation of monolayer lipid membrane 18. Bilayer membrane (BLM) 14, having a constitution resembling an organic cell membrane, is composed by the above-mentioned alkanethiol monolayer membrane 16 and monolayer lipid membrane 18.

In the present first embodiment, gel-like layer (to simply be referred to as a gel layer) 22 is formed on the surface of the above-mentioned BLM 14, namely on the side of monolayer lipid membrane 18 of the second layer of BLM 14. In addition, polymer layer 20, having polar groups, is adsorbed and formed between the surface of monolayer lipid membrane 18 and this gel layer 22. Here, lipid having "positive" or "negative" polar groups or non-polar lipid may be used as lipid of the monolayer lipid membrane 18. In the case of using phospholipid, in which the polar groups are negative, for the lipid of the monolayer lipid membrane 18, an amino acid having positive polar groups such as the polylysine, more specially poly-L-lysine shown in chemical formula (1) [mean value of n=41] below, for example, is used for polymer layer 20, which is adsorbed and formed on monolayer lipid membrane 18.

[Chemical 1]

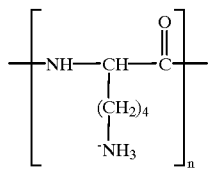

As is the case with this poly-L-lysine for example, when polymer layer 20 having the opposite polarity of, for example, phosphatidylserine contained in soybean phospholipid in monolayer lipid membrane 18 is provided on the surface of membrane 18, their mutual positive and negative polar groups interact resulting in a state in which the principal polymer chain of polymer layer 20 envelops the polar groups of monolayer lipid membrane 18. According to this type of mechanism, if a constitution results that immobilizes BLM 14 as a result of polymer layer 20 covering the surface of BLM 14 using poly-L-lysine, the stability of BLM 14, in other words the life-span of the BLM, can be improved. In addition, the use of an amino acid for polymer layer 20 enables the environment in the bilayer membrane to more closely approximate that in the biological condition.

In addition, gelled agarose, which is a type of sugar [chemical formula: (C$_6$H$_{10}$O$_5$.C$_6$H$_8$O$_4$)$_n$], is specifically used for the above-mentioned gel layer 22 formed on the surface of polymer layer 20. The material of the gel is not limited to agarose, however, and any material may be used provided it resembles the biological environment, remains stable for a long time, and is able to maintain a gel state. Also, it is preferable to use the above-mentioned hydrogel containing electrolyte solution as a gel from the aspect of realizing an environment which resembles the biological environment so as to activate protein. Thus, BLM 14 can be immobilized more reliably by further providing gel layer 22 on the surface of polymer layer 20, thereby further improving the life-span of BLM 14. Furthermore, the surface of BLM 14 may also be covered with gel layer 22 directly. The bilayer membrane device shown in FIG. 4 is arranged upright in a single unit with the substrate in an aqueous solution (membrane electrolyte solution to be described later). Consequently, as compared with the case of arranging a device horizontally as in the constitution of the prior art as shown, for example, in FIGS. 3A and 3B, peeling of only monolayer lipid membrane 18 of the second layer (monolayer membrane 2 corresponds to membrane 18 in FIGS. 3A and 3B) due to buoyancy effects can be prevented.

In addition, use of gel layer 22 for the layer that covers BLM 14 directly or indirectly by means of polymer layer 20 enables membrane electrolyte solution to be kept around BLM 14, thus making it possible to supply electrolyte solution required in the case of activating BLM 14 or protein introduced into its membrane. Moreover, due to the presence of this gel layer 22, disturbance of the membrane is prevented since movement of aqueous solution on the surface of BLM 14 is restricted, thereby increasing the life-span of the membrane.

Figures 3A, 3B:
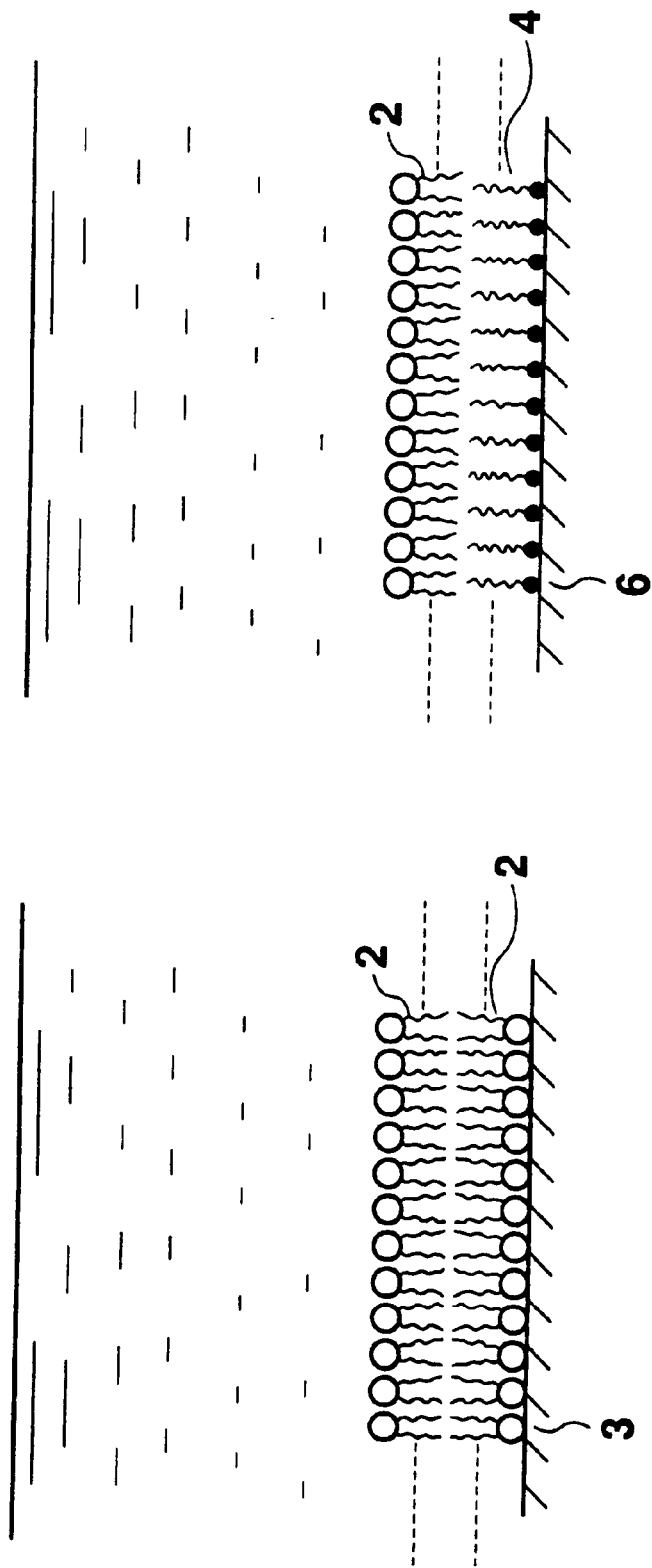
FIGS. 3A and 3B are drawings indicating the constitution of a different bilayer membrane device of the prior art.

More specifically, in contrast to a bilayer membrane obtained in the constitution of the prior art as shown in FIGS. 3A and 3B that has a life-span of several hours to just over ten hours, a bilayer membrane 14 as shown in FIG. 4 has a life-span of roughly 20 hours.

[Device Production Method]

Figure 1:
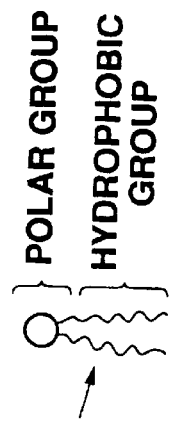

Next, the following provides an explanation of one example of a method for producing the bilayer membrane device shown in FIG. 1.

(1) Lipid and Decane Solution Preparation

In this embodiment, phospholipid, and more specifically soybean phospholipid containing 47% phosphatidylcholine (product name: Sigma type IV-S) is used for the previously described lipid, and this soybean phospholipid is partially purified in accordance with the method of Kagawa and Racker.

More specifically, this purification can be carried out according to the procedure described below.

i) First, acetone is added to phospholipid (10 mg) followed by allowing it to stand overnight at ordinary temperature.

ii) Next, the acetone is discarded and aspiration drying is performed for roughly 10 minutes with a rotary evaporator.

iii) Following evaporation, a small amount of diethyl ether is added to dissolve the lipid after which drying treatment is performed in the same manner as step ii) above.

iv) After drying by repeating the treatment of step iii) above several times, aspiration drying is performed for 30 minutes with a rotary pump.

v) Finally, n-decane (1 ml) is added to dissolve the purified phospholipid in the decane.

Furthermore, although phospholipid is used for the lipid, the lipid that can be used is not limited to that used here. The type of lipid used can be suitably selected according to compatibility with the protein ultimately introduced into the bilayer membrane, the environment in which the device is placed and so forth.

(2) Production of Substrate 13

A cover glass used for observation of biological samples is washed, and Au layer 12 is formed by sputtering at a thickness of approximately 100 nm on the glass to obtain substrate 13. However, the glass substrate 10 shown in FIG. 4 is not limited to a cover glass. Furthermore, Au layer 12 that is deposited should be formed to have a prescribed pattern having apertures (e.g., lattice or mesh pattern) or a prescribed thickness as necessary. In addition, Ag may be used instead of Au, and an Au substrate or Ag substrate may be used directly for the substrate. In the case of using Ag for the metal substrate or the metal layer on the substrate surface, however, since the electrolyte solution causes elution of an Ag substrate or Ag membrane when at a positive potential, the potential of the Ag substrate or Ag membrane must be controlled so as not to be positive.

(3) Formation of Bilayer membrane i) An ethanol solution (10 mM) of stearylmercaptan (SM) is prepared, and the substrate 13 prepared according to the above-mentioned section (2) is immersed in this solution and allowed to stand overnight at roughly 30° C.

During the time the substrate is allowed to stand, the Au on the substrate surface and the mercapto groups (—SH) of the stearylmercaptan react resulting in the occurrence of Au—S bonding. A monolayer with alkyl-chain which is, in this case, a monolayer SM membrane, namely alkanethiol monolayer membrane 16, is formed on the surface of Au layer 12 of FIG. 4 as a result of this Au—S bonding.

ii) A substrate on which alkanethiol monolayer membrane 16 is formed is attached in a predetermined cell, and a suitable amount (40 µl) of decane solution containing the phospholipid prepared in (1) above (concentration: 20 mg/ml) is dropped onto alkanethiol monolayer membrane 16 and allowed to stand for roughly 2 minutes. As a result, monolayer lipid membrane 18 is adsorbed and formed on alkanethiol monolayer membrane 16 as shown in FIG. 4.

iii) After forming monolayer lipid membrane 18, 10 µl of a polymer solution containing dissolved amino acid in the form of poly-L-lysine as polymer is added to the cell (concentration: 1 mg/ml). As a result, the positive polar groups of poly-L-lysine (—NH$_3$) are adsorbed onto the negative polar groups of monolayer lipid membrane 18 causing the poly-L-lysine in the form of polymer layer 20 to cover monolayer lipid membrane 18, thereby immobilizing and protecting monolayer lipid membrane 18.

(4) Preparation of Agarose Gel i) A gel (product name: Agarose, Sigma VII) having a low melting point (30° C. or lower) is dispersed in electrolyte solution (membrane system solution, namely a solution having the same components as that used for the aqueous solution that keeps a bilayer membrane flexible) to a concentration of several percent by weight (2.5% by weight).

ii) This electrolyte solution is stirred while heating and, after bringing to a boil, is then cooled to roughly 30° C.

iii) Membrane system electrolyte solution is injected into the cell in which the device is placed after polymer layer formation has been completed, and, after preheating the membrane electrolyte solution to at least 30° C., this membrane electrolyte solution is replaced with the agarose solution obtained in step ii) above.

iv) The agarose gel inside the cell is returned to ordinary temperature while stirring using a stirrer. The agarose forms a gel during the course of returning to ordinary temperature in this manner. Accordingly, after forming polymer layer 20, agarose gel layer 22 is formed on the surface of polymer layer 20.

Polymer layer 20 on the surface of BLM 14, and additionally agarose gel layer 22 on its surface, are therefore formed according to the above-mentioned procedure to obtain the bilayer membrane device of the present embodiment. The bilayer membrane is kept sufficiently flexible for protein in the membrane to function by placing the device obtained in the above manner in a predetermined cell, and arranging in the above-mentioned membrane electrolyte solution, an example of which is 0.1 M KCl; (pH 7.2). Here, since a polymer layer and agarose gel layer are provided as reinforcing materials of BLM 14, a bilayer membrane is obtained that has a longer life-span than bilayer membranes of the prior art as previously described.

Here, it is preferable that the agarose concentration of agarose gel, which is hydrogel, be low but within a range that enables the bilayer membrane to be immobilized. If the gel concentration is excessively high, there will cause finer mesh within the gel layer making the layer excessively rigid. Although this increases the resistance of the membrane to external impacts, due to the decreased water content, the movement of materials and ions within the gel layer, that are required by proteins and the bilayer membrane device to function is inhibited.

In addition, in the case of detecting an external material using proteins by introducing proteins into the bilayer membrane or by adsorbing liposomes having proteins within their membrane to the bilayer membrane as will be described later, it is necessary for the detected target material to reach the proteins by passing through the gel layer 22. From this aspect, it is preferable that gel layer 22 be as thin as possible provided its ability to immobilize the bilayer membrane is not lost.

Embodiment 2

In this second embodiment, a constitution is provided that further improves the life-span of the bilayer membrane when the structure of a bilayer membrane device as shown in the above-mentioned first embodiment is used, and that device is arranged upright in an aqueous system. The following provides an explanation of that embodiment with reference to FIGS. 4, 5, 6, and 7. Furthermore, the same reference numerals are used for those portions of the present embodiment that correspond to those members previously explained, and an explanation of those members will be omitted.

[Constitution]

Figure 5:
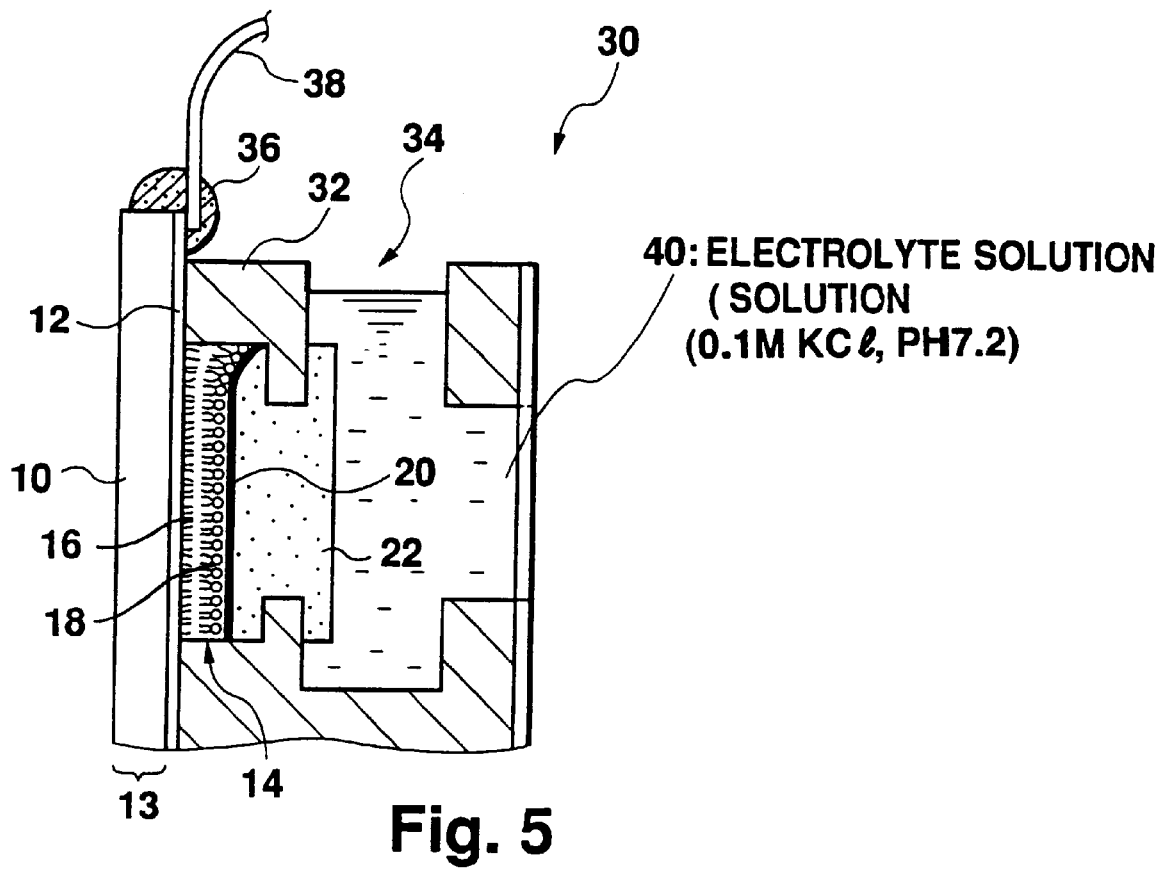
FIGS. 5, 6, and 7 are drawings indicating the constitution of a bilayer membrane device according to a second embodiment of the present invention.

Alkanethiol monolayer membrane 16 is formed in advance by Au—S bonds on the surface of substrate 13, and this substrate 13 is attached to cell 30 composed of Teflon in which liquid reservoir 34 is formed as shown in FIG. 5.

Membrane supporting portion 32 is provided protruding into cell reservoir 34 of cell 30 so as to extend towards the direction of BLM thickness on the side of substrate 13 on which BLM 14 is formed, and in the state in which this substrate 13 is attached within this cell 30.

In addition, reservoir 34 of cell 30 is able to be filled with each of the solutions for formation of monolayer lipid membrane 18, polymer layer 20, and agarose gel layer 22 indicated in the first embodiment. With substrate 13 attached within cell 30, each of the solutions are placed in reservoir 34 by following the procedure of the first embodiment, and a bilayer membrane device having the constitution shown in FIG. 4 is formed on the surface of substrate 13 by performing membrane formation treatment. Moreover, after formation of the device, electrolyte solution 40, an example of which is 0.1 M KCl (pH 7.2) is placed in reservoir 34 as shown in FIG. 5.

Next, an explanation is provided of the function of membrane supporting portion 32, a characteristic of the present second embodiment. As is shown in FIG. 5, a bilayer membrane device, which is attached to cell 30 and exposed to electrolyte solution 40, attempts to separate from alkanethiol monolayer membrane 16 as a result of a monolayer lipid membrane 18 positioned on the upper portion of bilayer membrane 14 being strongly affected by buoyancy. Here, if membrane supporting portion 32 as shown in FIG.

5 is not present above bilayer membrane 14, the separated monolayer lipid membrane 18 ends up flowing into electrolyte solution 40. If the lipid molecules are allowed to flow into electrolyte solution 40, bilayer membrane 14 is rapidly destroyed due to severe disturbance of the arrangement of its second layer.

In the present second embodiment, however, by arranging membrane supporting portion 32 protruding above bilayer membrane 14, lipid molecules are prevented from flowing into electrolyte solution 40. Furthermore, as shown in Embodiment 1, even if the surface of BLM 14 is covered with amino acid polymer layer 20 and agarose gel layer 22, the polymer and agarose are adsorbed and formed on the surface of BLM 14 not with strong chemical bonds, but rather through intermolecular force and physical adsorption alone. Thus, the use of this constitution makes it difficult to completely prevent the separated lipid molecules from flowing into the solution.

If the flow of lipid molecules into electrolyte solution 40 is prevented by providing membrane supporting portion 32, lipid molecules released from the alkanethiol monolayer membrane in the upper portion of BLM 14 are stopped below this membrane supporting portion 32 as shown in FIG. 5. A state of equilibrium is then reached between the lipid molecules released from BLM 14 and the lipid molecules supplied from the accumulation of lipid molecules below membrane supporting portion 32, and this is thought to result in stabilization of the BLM.

The amount of protrusion of membrane supporting 32 in the direction of width of BLM 14 is required to be at least the thickness of BLM 14 (the thickness of BLM 14 is normally 6–7 nm) in order to enable it to fully demonstrate its membrane supporting function.

Figure 6:
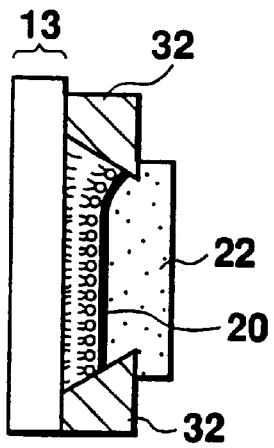
Figure 7:
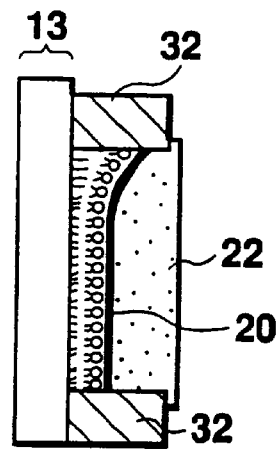

With respect to the shape of membrane supporting portion 32, if it is formed into the shape of an inverted letter "L" as shown in FIG. 5 so as to surround the top of BLM 14, the outflow of lipid molecules can be prevented more reliably. In addition, it may also have a shape that causes it protrude downward as it moves away from substrate 13 as shown in FIG. 6. Moreover, it may also simply be in the shape of a rectangle that extends in the direction of membrane thickness of the BLM as shown in FIG. 7 provided it protrudes by a sufficient amount.

In addition, although it has been previously explained that Teflon is used for the material of cell 30 and membrane supporting portion 32 integrated into a single unit with cell 30, this material is not limited to Teflon, but rather any material may be used provided it has resistance to each type of BLM forming solution and electrolyte solution. Furthermore, it is preferable that at least the surfaces of these constituents be hydrophobic and non-polar from the aspect of not having an effect on the BLM. If the surface of the membrane supporting portion demonstrates polarity, the polar groups of the lipid molecules will be attracted to this membrane supporting portion, thus resulting in the possibility of disturbance of the monolayer lipid membrane.

[Property Evaluation Results]

Next, an explanation is provided of the results of evaluating the properties of the bilayer membrane device provided with a membrane supporting portion. For this evaluation, a bilayer membrane which consists of an alkanethiol monolayer membrane and a molecular lipid membrane absorbed in the alkanethiol monolayer membrane, formed on substrate 13 having a metal layer, is used. Additionally, the properties of the bilayer membrane device covered with the polymer layer contained poly-L-lysine is evaluated.

Figure 8:
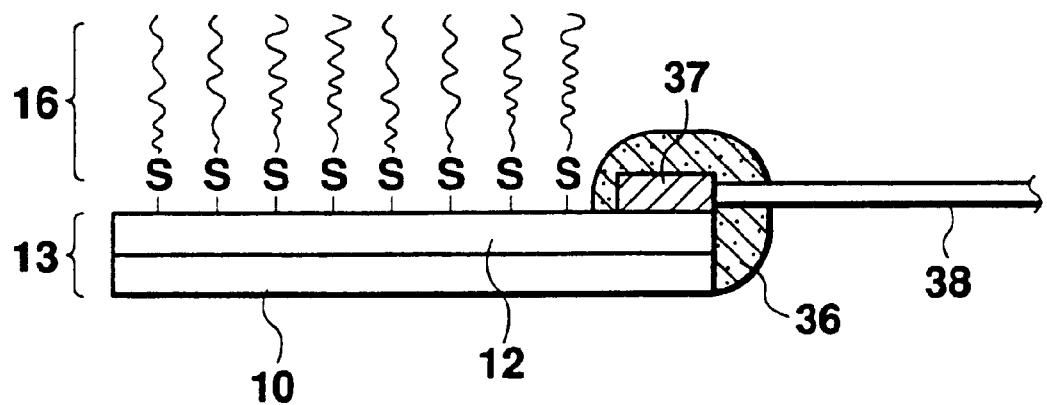
FIG. 8 is a drawing indicating the constitution of a sample used for evaluating the properties of a bilayer membrane device of the present invention.

First, alkanethiol monolayer membrane 16 is formed on the Au surface of substrate 13 as shown in FIG. 8 using steps (i) through (iii) of the procedure explained in Embodiment 1. Next, platinum (Pt) wire 38 is connected to Au layer 12 using silver paste 37. After drying silver paste 37, the connection between Pt wire 38 and Au layer 12 is reinforced by coating with epoxy resin 36. The completed assembly is allowed to stand until epoxy resin dries and hardens to obtain the sample shown in FIG. 8.

After forming the above-mentioned sample, it is placed in cell 30 as shown in FIG. 5, and 30–40 $\mu$l of lipid solution (decane solution) is added to the surface of the substrate of the sample, namely the surface of alkanethiol monolayer membrane 16 after which it is allowed to stand in this state for roughly 2 minutes to allow alkanethiol monolayer membrane 16 to conform to the lipid molecules in the solution.

Next, electrolyte solution (0.1M KCl buffer solution) 40 is placed in reservoir 34 of cell 30, after which the alternating current impedance between the silver-silver chloride electrode and the Au electrode using Au layer 12 of substrate 13 connected via a salt bridge is measured at prescribed time intervals. The measurement results will be shown in FIG. 10. Further, FIG. 11 shows the results of measuring the alternating current impedance when a poly-L-lysine (PLL) solution is placed in reservoir 34 after placement of electrolyte solution (for example, 10 hours after the placement of electrolyte solution).

(Measurement Result 1: substrate+alkanethiol monolayer membrane+monolayer lipid membrane)

Figure 9:
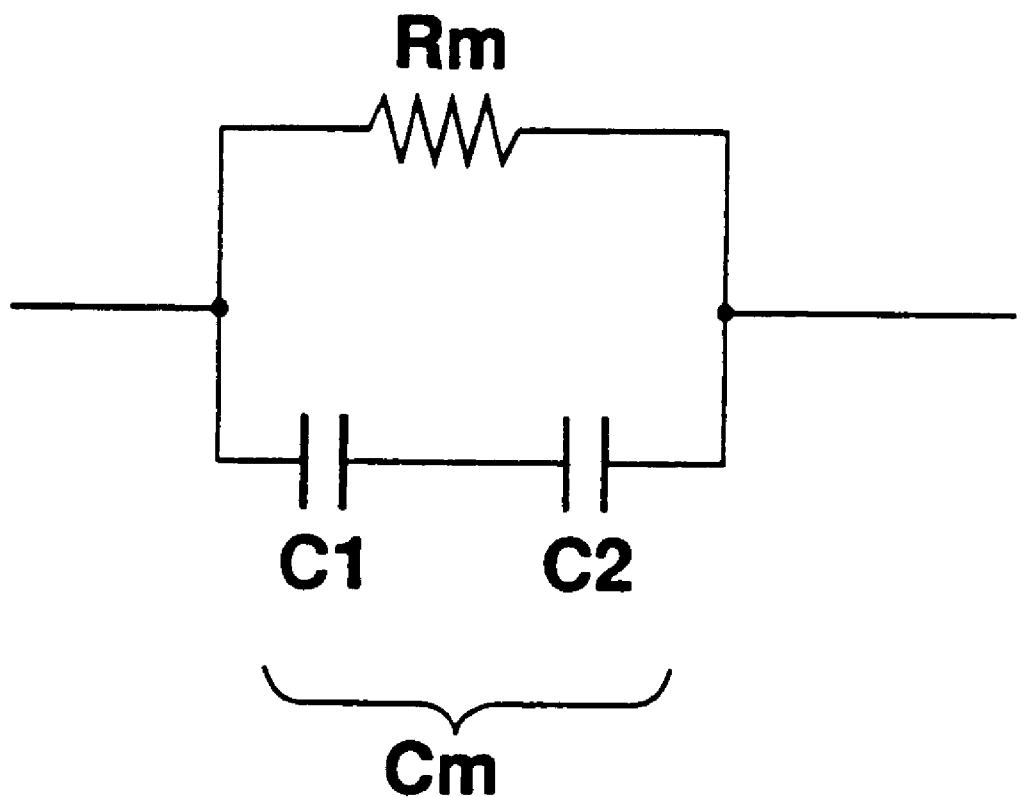
FIG. 9 is a drawing indicating an equivalent circuit of a bilayer membrane of a bilayer membrane device of the present invention.

FIG. 9 shows the membrane system equivalent circuit. In FIG. 9, $C_1$ indicates the characteristic capacitance of alkanethiol monolayer membrane 16, namely the capacitance in the state in which a second layer monolayer membrane is not present. In addition, $C_2$ is the capacitance of the second layer monolayer lipid membrane, while Rm is the membrane resistance of the bilayer membrane. As is shown in this equivalent circuit, capacitance $C_1$ of the first layer monolayer membrane 16 of the bilayer membrane and capacitance $C_2$ of the monolayer lipid membrane are connected in series between the silver-silver chloride electrode and the Au electrode, and the total capacitance of these two capacitances, namely bilayer membrane capacitance Cm, and membrane resistance Rm are connected in parallel between the silver-silver chloride electrode and the Au electrode.

Figure 10:
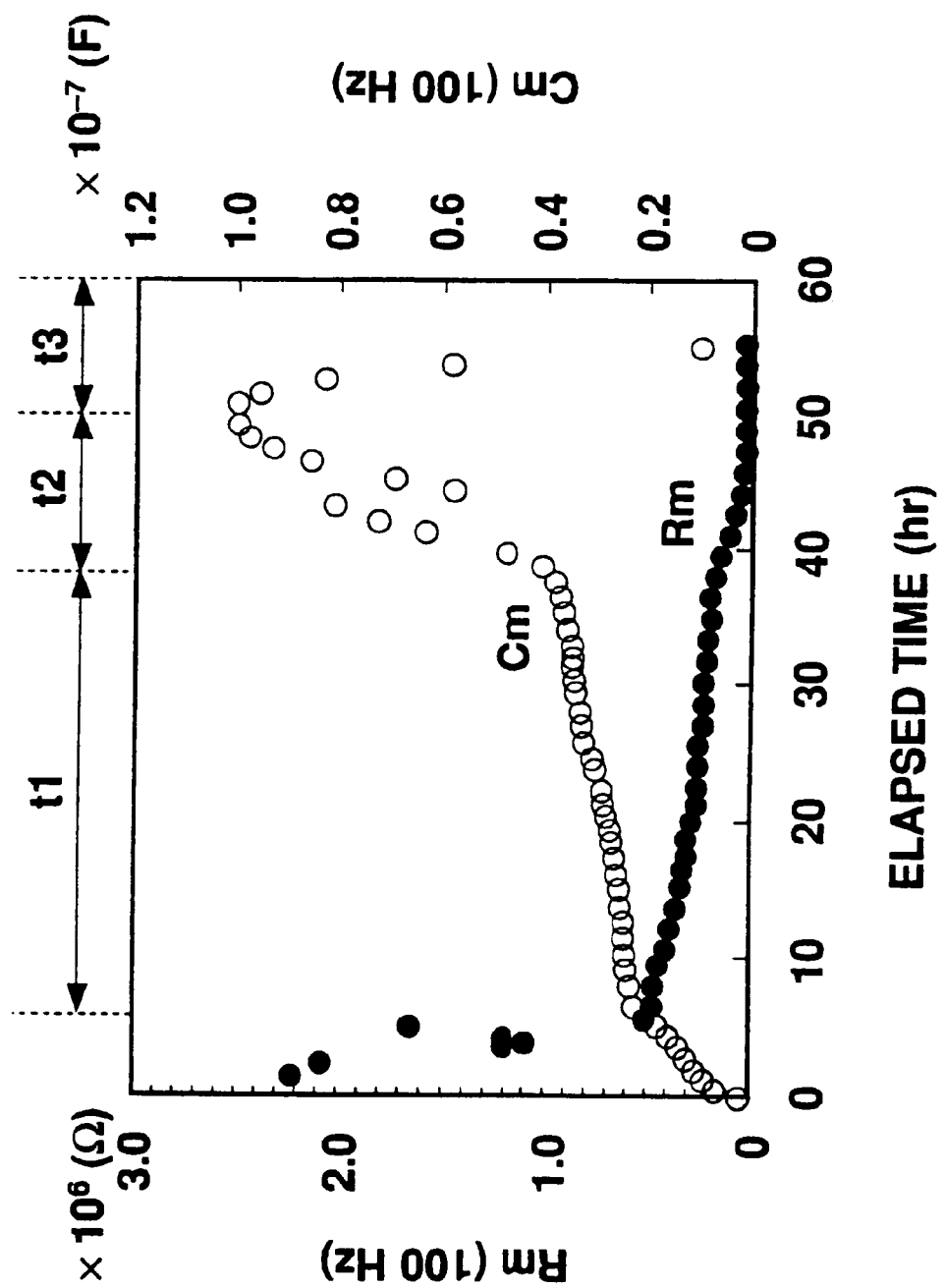
FIG. 10 is a drawing indicating the changes over time in membrane resistance and membrane capacitance as measured using the sample shown in FIG. 8.
Figure 11:
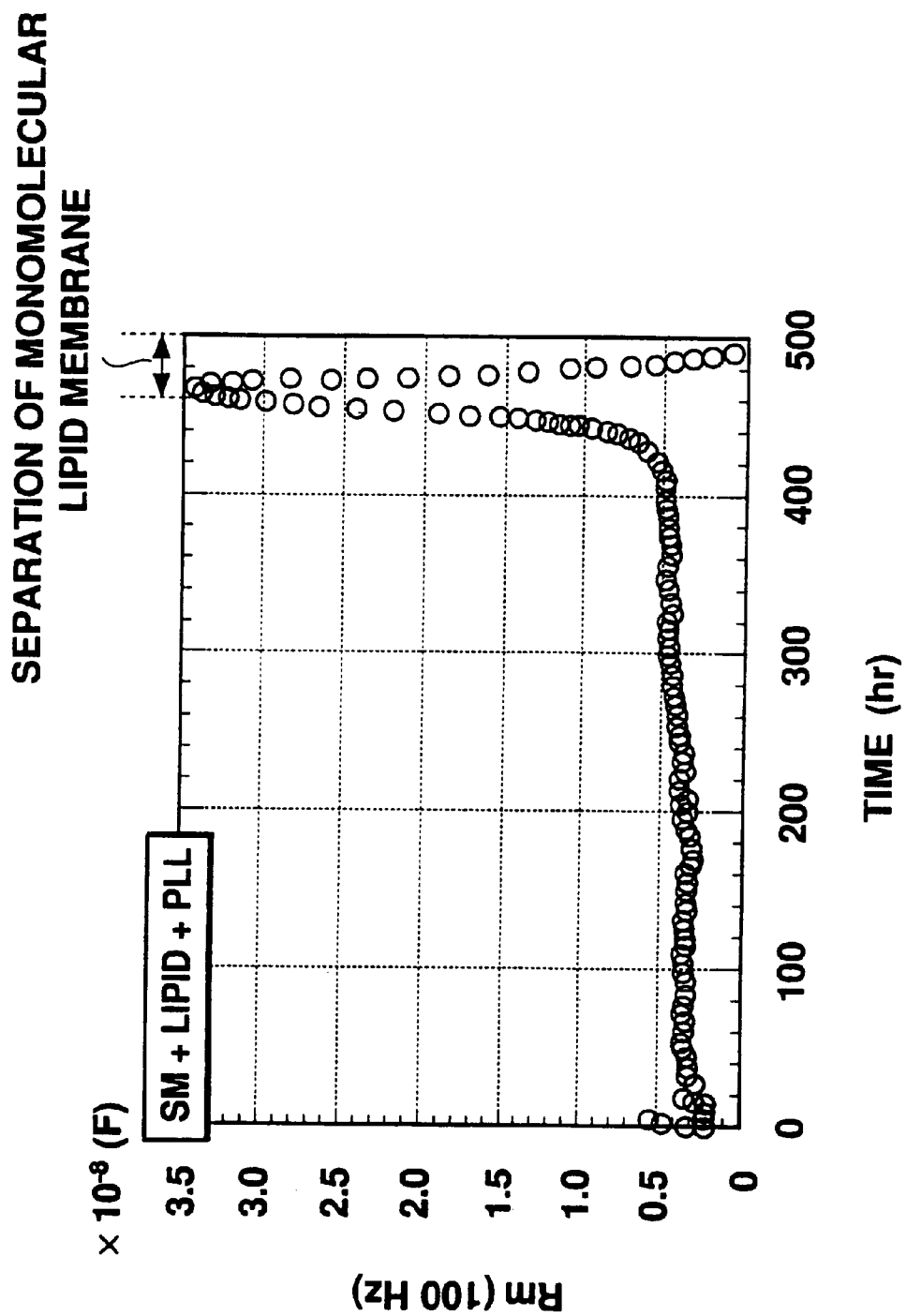
FIG. 11 is a drawing indicating the changes over time in membrane capacitance in a case where a PLL polymer solution is introduced into a system under the condition similar to that of FIG. 10.

FIG. 10 indicates the changes over time in membrane resistance and membrane capacitance between the above-mentioned silver-silver chloride electrode and Au electrode as measured at 100 Hz. In FIG. 10, elapsed time (hr) is represented on the horizontal axis, membrane resistance Rm ($\times 10^6$ $\Omega$) on the left vertical axis, and bilayer membrane capacitance Cm ($\times 10^{-7}$ F) on the right vertical axis. During period t1 starting from the start of measurement (t=0), namely from the time point when electrolyte solution 40 is placed in cell 30, until roughly 40 hours elapse, the lipid membrane present on the surface of alkanethiol monolayer membrane 16 gradually becomes thinner. Although both membrane resistance Rm and membrane capacitance Cm remain essentially constant during this period t1, membrane capacitance Cm increases somewhat since, for example, the layer of lipid decane solution becomes thinner and approaches the state of a bilayer membrane.

After 40 hours have elapsed, during period t2 from 40 to 50 hours after the start of measurement, membrane capacitance Cm increases rapidly due to an increase in the region of the bilayer membrane state.

Here, calculation of membrane resistance and membrane capacitance assuming that a bilayer membrane is formed on a whole Au surface and using each of the normal values of a bilayer membrane per unit area, specific membrane capacitance of [$Cm=500$ $nF/cm^2$] and Au electrode surface area of (=0.78 $cm^2$) results in membrane capacitance $Cm=390$ nF. The specific membrane resistance [Rm] and the membrane resistance Rm of the bilayer membrane varies with different membrane constitution, and may be [$Rm=200$ $M\Omega*cm^2$], for example, and Rm is for example $Rm=256$ $M\Omega$.

During the above-mentioned period t2, membrane capacitance is a maximum of $Cm=100$ nF. Membrane resistance Rm is, for example, $Rm=0.1$ $M\Omega$. Thus, the bilayer membrane can be estimated to account for roughly 25% of the electrode surface area by comparing the results of the above-mentioned calculations and this membrane capacitance. Furthermore, since the portion that does not form a bilayer membrane is considered to have a membrane thickness that is extremely large in comparison with the bilayer membrane, the capacitance of that portion can be ignored.

In addition, membrane capacitance Cm becomes small after 50 hours have elapsed in FIG. 10. This is thought to be the result of peeling of the monolayer lipid membrane that comprises the second layer of the BLM causing the alkanethiol monolayer membrane to be exposed on the surface. Actually, since membrane capacitance $C_1$ of the alkanethiol monolayer membrane is approximately 5 times greater than when the monolayer lipid membrane is present, separation of the second monolayer membrane causes membrane capacitance Cm to increase. At the set frequency for measurement (100 Hz) in FIG. 10, however, the value of membrane capacitance Cm decreases during period t3, since the actual capacitance does not work and therefore the detection current of this measurement apparatus exceeds a measurable range due to the decrease of resistance component and measurements thus become impossible.

In this manner, in the case of arranging a bilayer membrane, composed of an alkanethiol monolayer membrane and monolayer lipid membrane utilizing Au—S bonding on a substrate, upright in a prescribed aqueous system, it is possible to extend the life-span of the BLM to 20–40 hours by providing a membrane supporting portion.

(Measurement Result 2: substrate+alkanethiol monolayer membrane+monolayer lipid membrane+PLL layer)

FIG. 11 indicates the changes over time in membrane capacitance in the case of further placing a PLL solution in the system obtained similarly to the case of FIG. 10. Furthermore, measurement conditions are the same as those shown in FIG. 10, and in FIG. 11, membrane capacitance is also expressed as that between the above-mentioned silver-silver chloride electrode and metal electrode when measured at 100 Hz. In FIG. 11, elapsed time (hr) is represented on the horizontal axis, while capacitance of the bilayer membrane Cm ($\times 10^{-8}$ F) is represented on the horizontal axis.

According to FIG. 11, during the period until roughly 450 hours have elapsed, membrane capacitance Cm is stable. During this period, the bilayer membrane is covered with a polymer layer, and the state of the bilayer membrane can be thought to be maintained. In addition, when 450 hours have elapsed, an increase is observed in membrane capacitance Cm. As in the case shown in FIG. 10, the reason for the increase in membrane capacitance Cm is that the lipid membrane present on the surface of alkanethiol monolayer membrane 16 becomes thinner, thereby causing regions of a bilayer membrane state to increase. Peeling of the monolayer lipid membrane then occurs. Due to the resulting increase in actual membrane capacitance Cm in the same manner as FIG. 10, membrane capacitance decreases as shown in FIG. 11 under the conditions of the set frequency of 100 Hz because the detection current exceeds the measurable range due to the decreased resistance components.

On the basis of the above findings, in the case of arranging a bilayer membrane, composed of an alkanethiol monolayer membrane and monolayer lipid membrane utilizing Au—S bonding on a substrate, upright in a prescribed aqueous system, the life-span of the BLM can be further extended to roughly 450 hours under the conditions shown in FIG. 11 by providing a membrane supporting portion and also a polymer layer.

(Comparative Example of Bilayer membrane Life-span)

When measurements like that described above were performed while changing the respective constitutions of bilayer membranes, the life-span of each bilayer membrane was as shown in Table 1.

TABLE 1

| DEVICE CONSTITUTION | BLM LIFE-SPAN (PERIOD DURING WHICH ELECTRICAL PROPERTIES ARE STABLE) |
|---|---|
| WITHOUT MEMBRANE SUPPORTING PORTION | |
| (1) SM + LIPID + PLL LAYER + AGAROSE GEL LAYER | APPROX. 20 HOURS |
| WITH MEMBRANE SUPPORTING PORTION | |
| (2) BLM | 20 ~ 40 HOURS |
| (3) BLM + PLL LAYER | 100 ~ SEVERAL HUNDRED HOURS |
| (4) BLM + PLL LAYER + AGAROSE GEL LAYER | 1 MONTH OR MORE |

In Table 1, device constitution (1) is equivalent to the constitution shown in Embodiment 1, comprising a BLM formed by a monolayer membrane of SM (stearylmercaptan) and monolayer lipid membrane, the surface of which is covered with a polymer (PLL) layer and agarose gel layer, but not provided with the membrane supporting portion 32 shown in FIG. 5. In the case of this constitution (1), the BLM life-span is roughly 20 hours as determined in terms of the period during which electrical properties are stable. Consequently, in comparison with membrane life-span in the case of composing a BLM with a SM monolayer membrane and monolayer lipid membrane according to the prior art (just over ten hours at most), it is clear that a device is obtained that has a highly stable BLM as a result of the use of a gel layer.

Next, in the constitutions (2)–(4) shown in Table 1, the membrane supporting portion that characterizes the second embodiment is provided. More specifically, the device constitutions of (2)–(4) respectively consist of (2) a BLM composed of a SM monolayer membrane and a monolayer lipid membrane, (3) a BLM similar to that in constitution (2) having a PLL layer formed on its surface, and (4) a BLM similar to that in constitution (2) having a PLL layer and agarose gel layer formed on its surface. In the constitution (4), however, a liposome is actually provided between the PLL layer and the gel layer as shown in FIG. 10, which will be described later. As shown in Table 1, the life-span of the BLM is significantly extended in all of the constitutions of (2) through (4), reaching 20–40 hours in constitution (2), 100-several hundred hours in constitution (3), and one month or more in constitution (4). Thus, it is clear that the provision of a membrane supporting portion enables BLM stability to be dramatically improved in an aqueous system.

The use of device constitution (4), in which a gel layer is provided, enables obtaining a BLM having a life-span of one month or more, and a level of stability sufficient for use as a bilayer membrane device, and more specifically, a level of stability that is required for introduction of protein in that BLM followed by activation of protein function. Further, as is clearly understood by comparison of the constitution (4) with constitutions (2) and (3), the provision of a gel layer remarkably improves device life-span.

Embodiment 3

Figure 12:
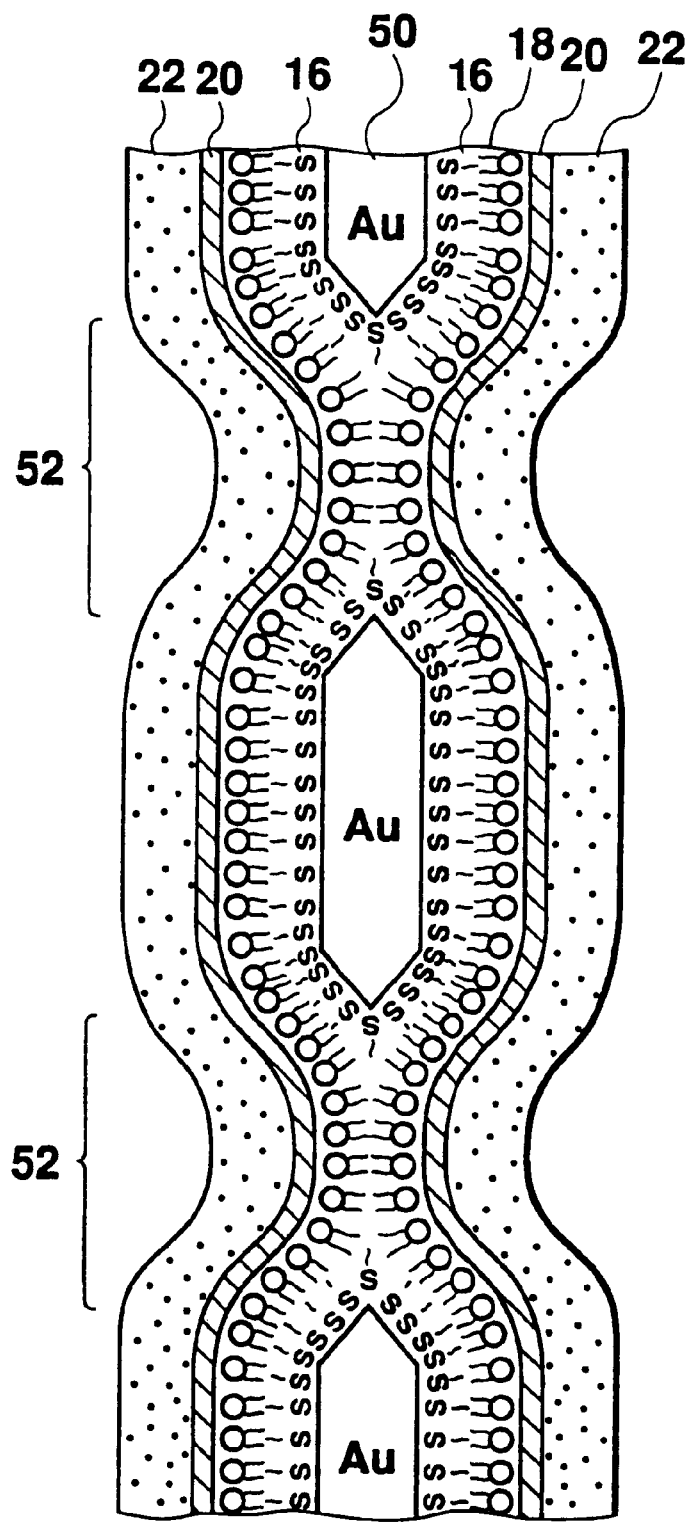
FIG. 12 is a drawing indicating the constitution of a bilayer membrane device according to a third embodiment of the present invention.
Figure 13B:
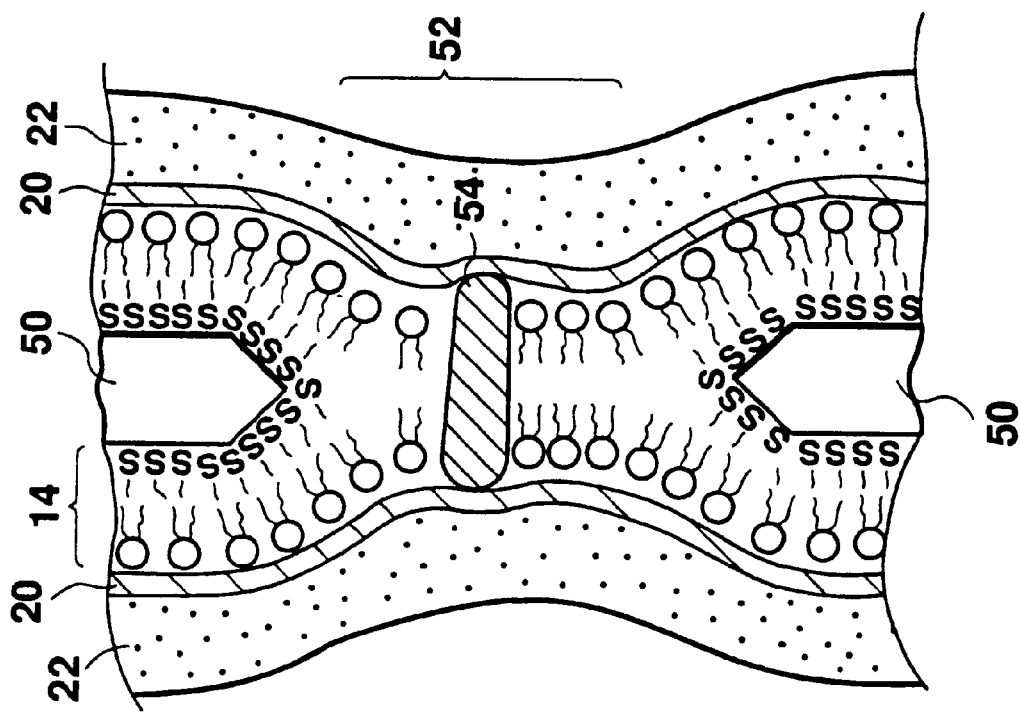
FIG. 13B is a cross sectional drawing of the bilayer membrane device shown in FIG. 13A.
Figure 13A:
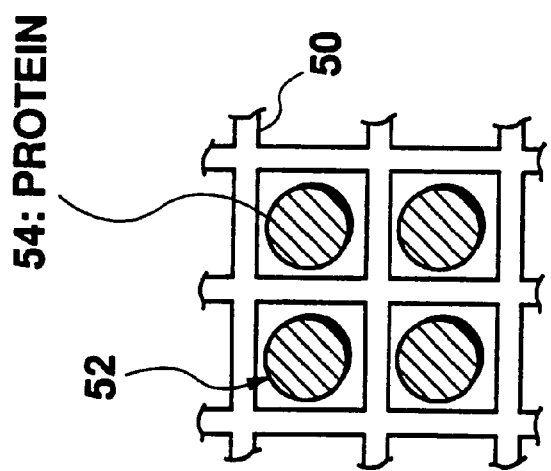
FIG. 13A is a conceptual plane drawing indicating the state in which protein is introduced into the bilayer membrane device shown in FIG. 11.

In the present embodiment, the substrate that forms the bilayer membrane has a structure having apertures, such as a lattice or mesh pattern, and the surface of the bilayer membrane is covered with at least a gel layer or is provided with a membrane supporting portion so as to increase the membrane stability. FIG. 12 indicates an example of the constitution of bilayer membrane device produced by using this type of substrate, while FIGS. 13A and 13B indicate a constitution in the case of introducing a protein in a bilayer membrane in the device shown in FIG. 12. Incidentally, the actual thickness of the substrates is thicker than that which is shown in FIGS. 12, 13A and 13B. Additionally, the configuration of the aperture formed on the substrate is not always limited to the configuration shown in the figures.

In the example of this third embodiment, lattice-shaped Au substrate 50 is used for the substrate, and, as shown in FIG. 12, alkanethiol monolayer membrane 16 is formed on the surface of Au substrate 50 by Au—S bonds. In addition, monolayer lipid (e.g. phospholipid) membrane 18 is adsorbed onto the surface of alkanethiol monolayer membrane 16 so as to surround it with its hydrophobic groups facing toward membrane 16, resulting in the formation of a bilayer membrane composed of alkanethiol monolayer membrane 16 and monolayer lipid membrane 18.

In addition, monolayer lipid membrane 18 composes a bilayer lipid membrane in this case, as a result of its hydrophobic groups mutually facing to the inside in gap regions 52 of Au substrate 50. Polymer (PLL) membrane 20 and agarose gel layer 22 are then formed on the surface of monolayer lipid membrane 18, namely the side having its polar groups, in the same manner as in the previously described embodiments.

As shown in FIG. 12, the stability of the membrane can be increased, as described above, by immobilizing the bilayer membrane with polymer layer 20 and gel layer 22. Moreover, gel layer 22 provided on the surface of bilayer membrane 14 is able to supply electrolyte solutions, which are required in the case of activating protein 54 that has been introduced into bilayer membrane 14, while immobilizing them around bilayer membrane 14. Further, disturbance of the membrane can be prevented since gel layer 22 stops movement of the aqueous system on the surface of bilayer membranes 14, thereby maintaining the bilayer membrane structure for a longer time and maintaining protein 54 in a state in which it is able to function.

When alkanethiol monolayer membrane 16 is formed on the surface of Au substrate 50 utilizing rigid Au—S bonds, alkanethiol monolayer membrane 16 is formed over the entire surface of Au substrate 50, making it more difficult to secure space for introducing protein by pushing back this monolayer membrane 16 from the back in the region in which this alkanethiol monolayer membrane 16 is formed. Therefore, by forming a bilayer membrane using a substrate having apertures, the hydrophobic groups of the second layer monolayer lipid membrane of the bilayer membrane formed on the surface of the substrate mutually face towards the inside of the bilayer membrane formed corresponding to gap regions 52 which are apertures of the substrate. Consequently, protein is easily introduced into the bilayer membrane at these gap regions 52 of the formed bilayer membrane.

In addition, as shown in FIGS. 13A and 13B, in the case of introducing protein 54 into bilayer membrane 14, protein 54 is first introduced into gaps 52 after forming bilayer membrane 14. Following this introduction, the surfaces of bilayer membrane 14 and protein 54 are covered with polymer layer 20 and agarose gel layer 22 to immobilize bilayer membrane 14 and introduced protein 54 from both sides of the membrane.

Furthermore, since the bilayer membrane device is arranged upright in an aqueous system as shown in FIG. 5, the life-span of the device can be further extended by providing a membrane supporting portion over the membrane to prevent lifting of monolayer lipid membrane 18 in an aqueous system as is indicated in Embodiment 2.

The substrate is not limited to the metal substrate 50 shown in FIGS. 12, 13A, and 13B, and may be a substrate having similar shape. For example, a glass substrate having a metal layer formed on its surface may be used.

Also, instead of the lattice-shaped substrate 50 as described above, other substrates, for example a plane glass substrate which does not have apertures and on which a metal material which bonds to the first monolayer membrane 16 is patterned into a form having apertures similar to those in substrate 50 in FIG. 13A (such as a lattice or mesh pattern) may be used. In the device shown in FIG. 14, a bilayer membrane is formed in thus formed substrate 13. In this case, as shown in FIG. 14, alkanethiol monolayer membrane 16 by Au—S bonding is not formed in the region where Au layer is absent. Thus, it is easy to introduce protein into that absence regions (gap regions).

Embodiment 4

Next, an explanation is provided of another example of a constitution of the bilayer membrane device shown in the first and second embodiments with reference to FIG. 15.

In FIG. 15, bilayer membrane 14, composed of an alkanethiol monolayer membrane and a monolayer lipid membrane, is formed on substrate 13, on at least the surface of which is formed an Au layer (In FIG. 15, however, the metal layer formed on substrate surface is not shown). In the present fourth embodiment, amino acid polymer (PLL) membrane 20 is provided on the surface of bilayer membrane 14 in the same manner as in Embodiment 1, and liposomes 60, having protein 54 within their membranes, are adsorbed to the surface of this polymer layer 20. As shown in the drawing, liposomes 60 have the bilayer membrane structure of monolayer phospholipid membrane 58, and polar groups (negative polar groups) of monolayer phospholipid membrane 58 are located on its outside surface. Thus, as a result of the polar groups of this monolayer lipid membrane 58 being attracted to the positive polar groups of polymer PLL, a liposome layer is adsorbed and formed on the surface of polymer layer 20. In addition, the stability of the device can be improved when agarose gel layer 22 is formed so as to cover the polyme layer 20 and this liposome 60 and immobilize bilayer membrane 14 and liposomes 60 on its surface. Furthermore, if a monolayer membrane is formed for the second layer of BLM 14 by using a lipid having positive polar groups, it is not necessary to dispose polymer layer 20 between BLM 14 and the liposome. In this case, the polymer layer may be formed between the liposome and agarose gel layer 22.

As has been described above, the environment of liposomes 60 can be made to more closely approximate that biological condition, the stability of liposomes 60 can be improved, and protein 54 can be made to function more normally and with greater stability by forming a liposome on bilayer membrane 14 and polymer layer 20 produced on a substrate by using those membranes and gel layer 22. Furthermore, since the bilayer membrane device shown in FIG. 15 is placed in an aqueous system, the stability of the membrane can be further improved by providing a membrane supporting portion above the membrane in the same manner as in Embodiment 2.

In each of the embodiments as explained above, the protein that is introduced into the bilayer membrane (containing liposomes) can be selected according to the specific application. In addition, it is preferable that suitable materials be selected for the materials that compose the substrate, bilayer membrane, polymer layer and gel layer in consideration of compatibility with the protein used and according to the environment in which the device is placed.

In addition, the bilayer membrane device of the present invention can be used as an optical sensor, odor sensor or various other types of sensors if a protein that changes in response to various stimuli is introduced into the membrane and activated.

Further, in the device shown, for example, in FIG. 14, it is possible to activate protein present at specific positions in a membrane and to detect changes in electrical property caused by the activation of protein, by using a metal material (Au layer 12) formed into a desired pattern such as matrix pattern (50) of FIG. 13A as an electrode for the support substrate of a bilayer membrane. Specifically, in a case where a bilayer lipid membrane device is composed of a light-sensitive protein, etc. contained in, for example, a highly halophilic microorganism and is used as an optical sensor, the metal on the substrate can be used as wiring.

What is claimed is:

1. A bilayer membrane device comprising:
   a substrate having a substantially vertical surface;
   a bilayer membrane formed on the surface of the substrate; and
   a membrane supporting portion for supporting an upper portion of said bilayer membrane, the membrane supporting portion being disposed adjacent the substrate and above the membrane, the membrane supporting portion having a surface extending in the direction of membrane thickness of said bilayer membrane and contacting the membrane.

2. A bilayer membrane device as set forth in claim 1 wherein said membrane supporting portion has a length equal to or greater than the membrane thickness of said bilayer membrane and inhibits lifting of said bilayer membrane arranged upright in an aqueous system.

3. A bilayer membrane as set forth in claim 1 wherein at least the surface of said membrane supporting portion that makes contact with said bilayer membrane is formed from a non-polar material.

4. The bilayer membrane device of claim 1, further comprising a polymer layer formed on the bilayer membrane.

5. A bilayer membrane device as set forth in claim 4 wherein a gel layer is formed on said polymer layer.

6. The bilayer membrane device of claim 5, further including liposomes arranged between the polymer layer and the gel layer.

7. The bilayer membrane device of claim 6, wherein the liposome has a phospholipid monolayer on the outside having a polarity, and wherein the polymer layer has a polarity opposite of that of the phospholipid monolayer of the liposome.

8. A bilayer membrane device as set forth in claim 5, wherein a hydrogel is used for said gel layer.

9. A bilayer membrane device as set forth in claim 5, wherein a sugar is used for said gel layer.

10. The bilayer membrane device of claim 1, wherein the membrane supporting portion stabilizes membrane by equilibrating molecules supplied from a molecule accumulation on the lower side thereof and molecules peeled off the bilayer membrane.

11. The bilayer membrane device of claim 1, wherein the supporting portion has an inverse L shape extending from the substrate in the thickness direction of the bilayer membrane and having a tip end bending downward.

12. The bilayer membrane device of claim 1, wherein the supporting portion is rectangular.

13. The bilayer membrane device of claim 1, wherein the supporting portion protrudes downwardly to a greater extent with increasing distance from the substrate.

14. The bilayer membrane device of claim 1, wherein the supporting portion comprises polytetrafluoroethylen.

15. The bilayer membrane device of claim 1, wherein said substrate is a metal substrate having apertures, a substrate with apertures and having a metal layer formed on its surface, or a substrate in which a metal layer of a predetermined pattern having apertures is formed on its surface;
   wherein the metal substrate or metal layer comprises a metal material that bonds with the monolayer membrane on the substrate side of said bilayer membrane;
   wherein a bilayer membrane is formed in the gap regions formed by said apertures of said substrate or said metal layer; and
   wherein the device further comprises protein in the membrane of said bilayer membrane formed in said gap regions.

16. A bilayer membrane device as set forth in claim 1, wherein said bilayer membrane is composed of an alkanethiol monolayer membrane, the polar groups of which are bonded to a metal material on the surface of said substrate; and a monolayer lipid membrane that is arranged with its hydrophobic groups facing toward said alkanethiol monolayer membrane.

17. A bilayer membrane device a s set forth in claim 1, wherein said substrate is a metal substrate or a substrate in which a metal layer is formed on its surface, and a metal material that bonds with the monolayer membrane on the substrate side of said bilayer membrane is used for said metal substrate or metal layer.

18. A bilayer membrane device as set forth in claim 1, wherein said bilayer membrane is a membrane for holding protein.

* * * * *